(12) United States Patent
Hung

(10) Patent No.: US 6,403,970 B1
(45) Date of Patent: Jun. 11, 2002

(54) MATRIX BIOCHIP SENSING SYSTEM

(75) Inventor: Lung-Yu Hung, Hsinchu (TW)

(73) Assignee: Industrial Technology Research Institute, Hsinchu (TW)

(*) Notice: Subject to any disclaimer, the term of this patent is extended or adjusted under 35 U.S.C. 154(b) by 50 days.

(21) Appl. No.: 09/729,104

(22) Filed: Dec. 5, 2000

(51) Int. Cl.[7] ............................................... G01N 21/64
(52) U.S. Cl. .......................... 250/458.1; 250/461.2; 356/317; 436/172
(58) Field of Search ........................ 250/458.1, 461.2, 250/461.1, 459.1; 356/318, 317, 417; 436/176

(56) References Cited

U.S. PATENT DOCUMENTS

| | | | |
|---|---|---|---|
| 4,707,454 A | * 11/1987 | Hendrix | 436/500 |
| 5,162,654 A | * 11/1992 | Kostichka et al. | 204/612 |
| 5,355,215 A | * 10/1994 | Schroeder et al. | 250/461.2 |
| 5,635,402 A | * 6/1997 | Alfano et al. | 250/459.1 |
| 5,991,030 A | * 11/1999 | Yamamoto et al. | 250/458.1 |
| 6,043,880 A | * 3/2000 | Andrews et al. | 250/361 C |
| 6,166,804 A | * 12/2000 | Potyrailo et al. | 250/458.1 |
| 6,271,042 B1 | * 8/2001 | Watson et al. | 250/458.1 |
| 6,310,687 B1 | * 10/2001 | Stumbo et al. | 250/458.1 |
| 6,329,661 B1 | * 12/2001 | Perov et al. | 250/459.1 |
| 6,352,672 B1 | * 3/2002 | Mabile et al. | 380/252 |
| 2001/0033374 A1 | * 2/2001 | Hoyt | 356/317 |

FOREIGN PATENT DOCUMENTS

EP        342979 A2 * 11/1989        .......... G01B/11/06

* cited by examiner

*Primary Examiner*—Constantine Hannaher
*Assistant Examiner*—Albert Gagliardi
(74) *Attorney, Agent, or Firm*—Bacon & Thomas, PLLC

(57) ABSTRACT

The matrix biochip sensing system of this invention uses a low-cost LED (light emit diode) matrix as the light source for the sensing system. The matrix biochip sensing system comprises an LED matrix light source, a biochip clamping member, an optical information filter module, an optical lens array, an optical sensor and a signal processing and control module. The light spots of the LED matrix is turned on in sequence, such that the fluorescent spots of the biochip that are respectively corresponding to the light spots of the laser diodes matrix may be actuated in the same sequence. Fluorescent spots so actuated are focused to a single optical sensor through an optical lens. At each sensing cycle of the optical sensor, only one fluorescent spot may be actuated. The output of the optical sensor in combination of the time axis may be processed by the signal processing and control module to obtain the genetic signals of the biochip.

5 Claims, 2 Drawing Sheets

MATRIX BIOCHIP SENSING SYSTEM

FIELD OF INVENTION

This invention relates to a matrix biochip sensing system, especially to a biochip sensing system employing a matrix light source.

BACKGROUND OF INVENTION

Recently the potential development of biotechnology and its contribution to human life has been a focus of discussion. Among all biotechnologies, the "biochip" in which genetic technology, molecular biology, electronic technology, electro-optical technology and chemical technology are combined, is playing a leading role. Many research and development institutes are involving the development of biochips and equipment and tools for such development.

In the development of the biochip, the integration of all necessary technologies and mechanisms in a miniature chip, such that the chip may be compact, low-cost and reliable, has become a major task of all researchers. MEMS (micro electro-mechanism system) technology is one such solutions to some of the above-said questions.

A "genetic chip" is a biochip that employs genetic technologies and provides functions such as diseases diagnosis or genetic performance variation studies. A genetic chip is prepared as a matrix wherein a variety of probes prepared with genetic fragments are positioned in their respective positions of the matrix Test samples or gene samples of a target are processed and applied to the genetic chip so that the gene fragments of the samples may be mixed or hybridized with the probes in the genetic chip. The hybridized productions of respective positions in the matrix then may be sensed by a testing system to determine the genetic information of the test samples.

Testing systems of the genetic chip include the confocal fluorescent laser scanner system and other applicable systems. The confocal fluorescent laser system first applies excitation signals to the hybridization products and then scans the fluorescent signals in the matrix under a laser source. In such a system the laser source is an expensive laser beam generator and the scanner is a highly sensitive photo multiplier tube scanner. A dot matrix image may thus be obtained and the image may then be reconstructed in a computerized image processing system such that analysis of the biologic information of the test samples may be achieved.

Due to the high cost of the confocal fluorescent laser scanner system, several substitutions to cost-down the sensing system of the genetic chip have been disclosed. Available systems include the direct image sensing system that provides to each probe position in the matrix an independent light source to actuate the florescence and employs a CCD (charge coupler device) sensor as the matrix image sensor. As the CCD sensor itself is a matrix sensor system, cost of the sensing system may thus be saved. However, due to the relatively low power of the florescence signals and the relatively strong power of the background noises, a complicated circuit is needed to remove the noises.

It is thus a need to provide a simplified biochip sensing system that can be manufactured under a lower cost.

It is also necessary to provide a novel biochip sensing system with improved preciseness.

It is also necessary to provide a biochip sensing system wherein background noises may be eliminated.

It is also necessary to provide a biochip sensing system whereby test procedure of biochips is made easier.

OBJECTIVES OF INVENTION

The objective of this invention is to provide a novel biochip sensing system.

Another objective of this invention is to provide a matrix biochip sensing system.

Another objective of this invention is to provide a simplified biochip sensing system that can be manufactured under a lower cost.

Another objective of this invention is to provide a novel biochip sensing system with improved preciseness.

Another objective of this invention is to provide a biochip sensing system wherein background noises may be eliminated.

Another objective of this invention is to provide a biochip sensing system whereby test procedure of biochips is made easier.

SUMMARY OF INVENTION

According to the matrix biochip sensing system of this invention, a low-cost LED (light emit diode) matrix is used as light source for the sensing system. The matrix biochip sensing system of this invention comprises an LED matrix light source, a biochip clamping member, an optical information filter module, an optical lens array, an optical sensor and a signal processing and control module. The light spots of the LED matrix is turned on in sequence, such that the fluorescent spots of the biochip that are respectively corresponding to the light spots of the LD matrix may be actuated in the same sequence. Fluorescent spots so actuated are focused to a single optical sensor through an optical lens. At each sensing cycle of the optical sensor, only one fluorescent spot may be actuated. The output of the optical sensor in combination of the time axis may be processed by the signal processing and control module to obtain the genetic signals of the biochip.

These and other objectives and advantages of this invention may be clearly understood from the detailed description by referring to the following drawings.

DETAILED DESCRIPTION OF INVENTION

Figure 1:
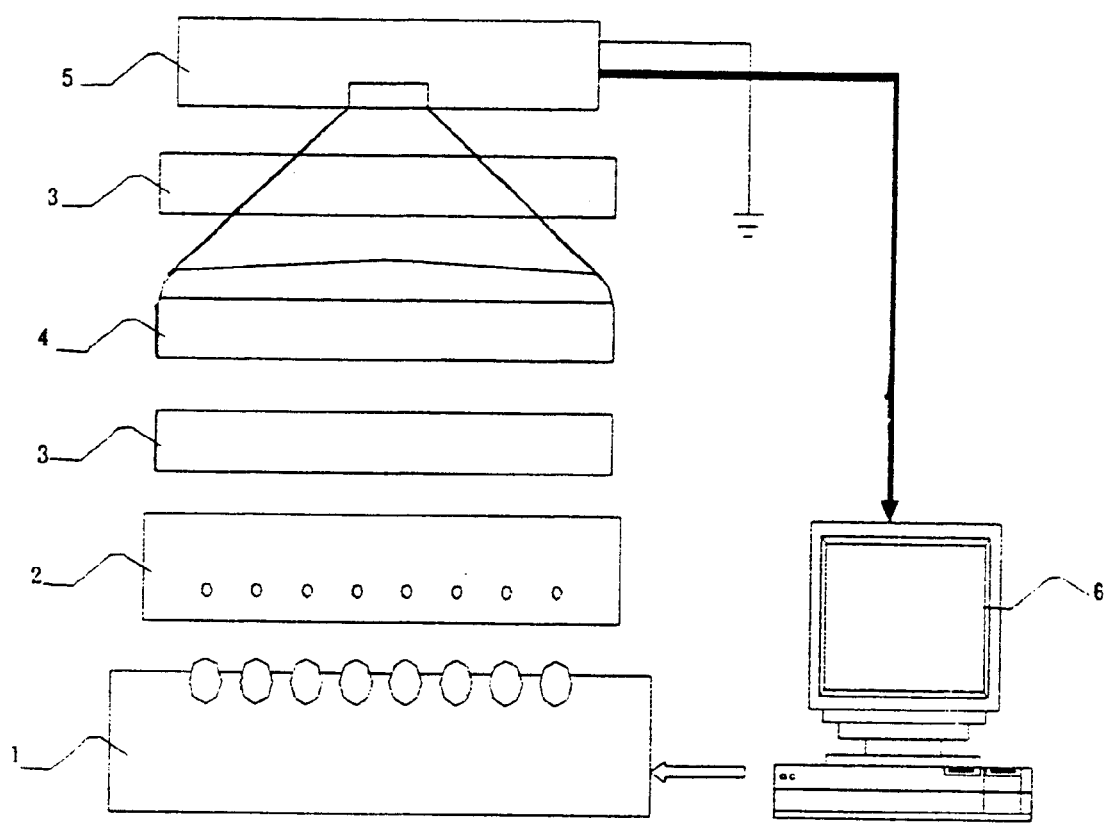
FIG. 1 illustrates the system diagram of the matrix biochip sensing system of this invention.

FIG. 1 illustrates the system diagram of the matrix biochip sensing system of this invention. As shown in this figure, the matrix biochip sensing system of this invention comprises an LED matrix light source 1, a biochip clamping member 2, an optical information filter module 3, an optical lens array 4, an optical sensor 5 and a signal processing and control module 6.

In sensing a biochip with the matrix biochip sensing system of this invention, a biochip is first positioned in the biochip clamping member 2. In the biochip is prepared a test sample matrix. In each spot of the test sample matrix, a genetic fragment sample is already reacted with respective probe and contains a fluorescent signal. According to this invention, all spots of the test sample matrix overlap with or are corresponding to respective spots of the LED matrix 1, directly or through an optical member (not shown). In order to achieve this purpose, it is possible to arrange replacement of the LED matrix 1 in different specifications.

In sensing the biochip, the signal processing and control module 6 generates actuation signals along a time sequence to drive the LED's of the LED matrix 1 to generate light in sequence. The light beam generated by the LED matrix 1 enters into respective spots of the test sample matrix of the biochip in the same sequence, such that the florescence of the test sample is actuated by the incident light and generates fluorescent light in sequence. The fluorescent light so generated is filtered by the optical filter module 3, such that the LED actuation light components may be filtered. The fluorescent light is then concentrated by the optical lens array 4 and reaches the optical sensor 5. In FIG. 1, the optical filter module 3 is positioned between the optical lens array 4 and the biochip clamping member 2, it may also be positioned between the optical lens array 4 and the optical sensor 5. The signal processing control module 6 measures the light power of the fluorescent light as sensed by the optical sensor 5, according to the working cycles of the LED matrix and a record is thus obtained and stored. The file so recorded may be processed with a conventional series to parallel processor (not shown) and a matrix genetic information file of the biochip may be obtained for further processing.

During the whole procedure in generating the LED light and measuring the fluorescent signals, respective signals are actuated by respective LED light source within respective time periods. The signal representing one fluorescent spot of the biochip so sensed may not be influenced by signals representing other fluorescent spots. The fluorescent light power of all matrix spots of the biochip may thus be enhanced.

In another embodiment of this invention, the environmental noise of the sensing system is taken for consideration. In doing this, the background noise when the LED matrix light source is OFF is sensed and used as the environmental noise to calibrate the power of the fluorescent light of all matrix spots of the biochip. Such an approach may be easily achieved by those skilled in the art and detailed description thereof is thus omitted.

Figure 2:
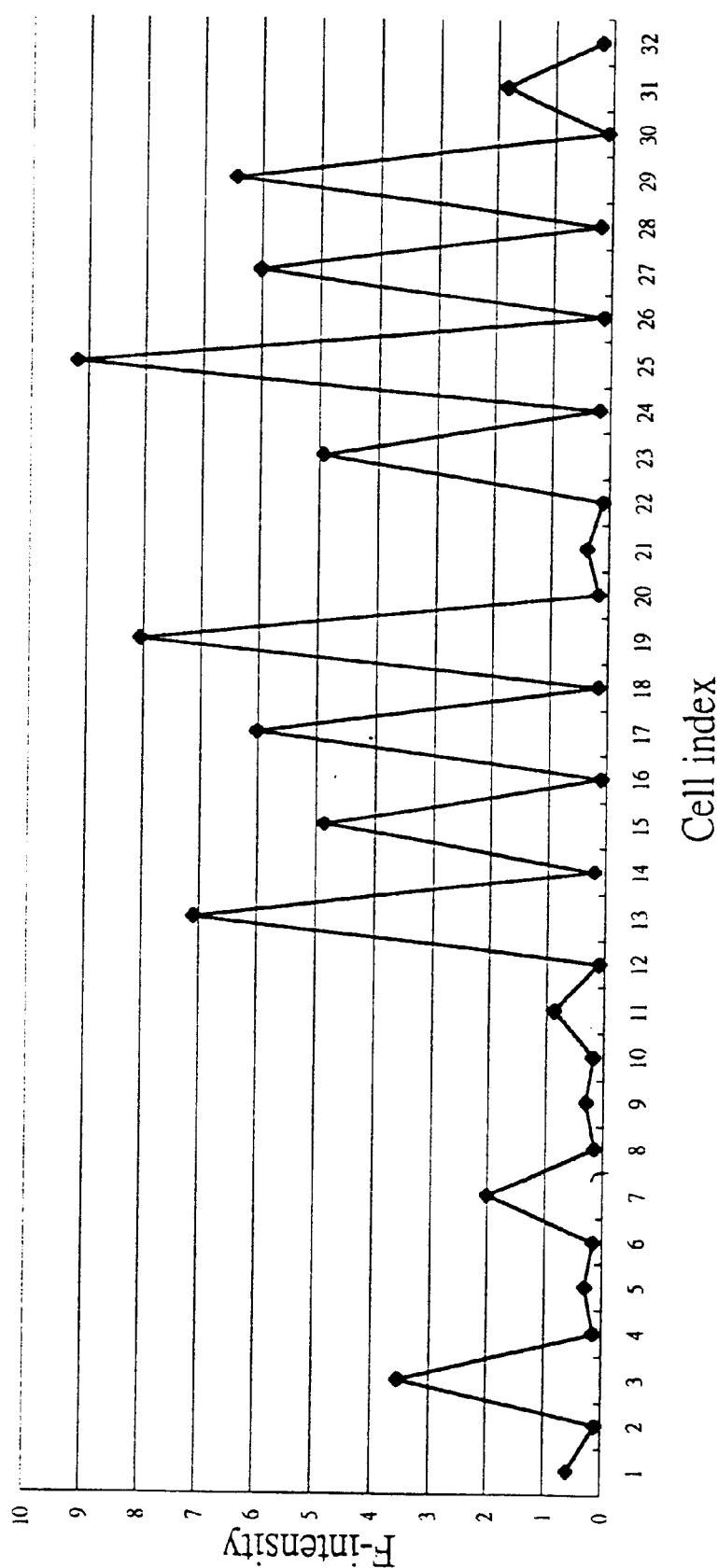
FIG. 2 shows the fluorescent signal power distribution of a biochip as tested under the matrix biochip sensing system of this invention.

FIG. 2 shows the fluorescent signal power distribution of a biochip as tested under the matrix biochip sensing system of this invention. In this figure, the power values in even numbers are values of fluorescent light signals when the LED light source is OFF.

In the above embodiments, the light source is an LED matrix light source. It is understood that any light source that is arranged as a matrix and generates light beams from respective elements of the matrix in a time sequence may be suited in this invention, as long as the light source is cost effective. In the present invention, the optical sensor may be a photo multiplier tube, a PIN optical diode, a silicon based optical sensor or a germanium based optical sensor. Of course, other optical sensors that are able to sense a fluorescent light are also applicable. The optical filter module may comprise a long pass filter, while other filters that can filter the light generated by the light source may be suited in this invention. As to the control of the light source, an electronic switching scanner may be applicable. A control program operated under a computer may also be applicable. As the schematic structure of the matrix biochip sensing system is disclosed, any variation may be realized by those skilled in the art.

EFFECTS OF INVENTION

As described above, the matrix biochip sensing system of this invention is able to generate a light beam for its corresponding fluorescent spot of the biochip at each working cycle. The fluorescent signals in the biochip may thus be sensed in sequence under a high speed. While the fluorescent signals of the biochip may be obtained directly, the signal power of each florescence spot of the biochip may not interfere with fluorescent light generated by other spots. Preciseness in the measurement of the biotech signals of the biochip may be improved.

The matrix biochip sensing system of this invention has a simplified structure and may be prepared under a relatively low cost. The specification and matrix distribution of the LED matrix light source may also be adjusted easily by replacing different LED matrix light sources. A dynamic biochip sensing system can thus be accomplished.

As the present invention has been shown and described with reference to preferred embodiments thereof, those skilled in the art will recognize that the above and other changes may be made therein without departing from the spirit and scope of the invention.

What is claimed is:

1. A matrix biochip sensing system, comprising:
   a matrix light source comprising a plurality of light generating spots arranged in a matrix wherein each light generating spot generates a light independently;
   a biochip clamping element, positioned in the downstream position relative to said matrix light source to position a biochip comprising a matrix distribution, wherein each spot of said matrix distribution of said biochip is spatially corresponding to one light generating spot of said matrix light source;
   an optical sensor to sense light power of respective spots of said matrix distribution of said biochip, after being actuated by light generated by said light generating spot of said matrix light source; and
   an optical signal processing and control module to control light generating from respective light generating spots of said matrix light source whereby only one light generating spot generates light during one working cycle, and to record time of light generation and light power as sensed by said optical sensor.

2. The matrix biochip sensing system according to claim 1, further comprising an optical filter module positioned between said matrix light source and said optical sensor to filter out most light generated by said matrix light source.

3. The matrix biochip sensing system according to claim 1, further comprising a light concentration module to focus light generated at said spots of said matrix distribution of said biochip into said optical sensor.

4. The matrix biochip sensing system according to any of claims 1 to 3, wherein said optical sensor is selected from the group of photo multiplier tube, PIN optical diode, silicon based optical sensor and germanium based optical sensor.

5. The matrix biochip sensing system according to any of claims 1 to 3, wherein said matrix light source is an LED matrix light source.

* * * * *